United States Patent [19]

Fleer

[11] 3,982,322

[45] Sept. 28, 1976

[54] ARRANGEMENT FOR THE SWITCHING ON-AND-OFF OF A PRESSURIZED MEDIUM FLOW

[75] Inventor: Ernst Otto Fleer, Bensheim-Auerbach, Germany

[73] Assignee: Siemens Aktiengesellschaft, Erlangen, Germany

[22] Filed: Sept. 4, 1975

[21] Appl. No.: 610,253

[30] Foreign Application Priority Data

Sept. 12, 1974 Germany............................ 2443708

[52] U.S. Cl................................... 32/22; 137/38
[51] Int. Cl.².......................................... A61C 19/02
[58] Field of Search.................... 32/22, 28, DIG. 3; 137/38, 39

[56] References Cited
UNITED STATES PATENTS

| | | | |
|---|---|---|---|
| 1,180,482 | 4/1916 | Flanders | 137/38 |
| 1,271,434 | 7/1918 | Claudel | 137/39 |
| 1,545,996 | 7/1925 | Asknen et al. | 137/38 |
| 2,703,582 | 3/1955 | Stepanian | 137/38 |
| 3,672,059 | 6/1972 | Booth | 32/22 |
| 3,718,972 | 3/1973 | Fox et al. | 32/22 |
| 3,740,852 | 6/1973 | Holmquist | 32/22 |
| 3,755,899 | 9/1973 | Betush | 32/22 |
| 3,778,903 | 12/1973 | Gardella et al. | 32/22 |
| R28,649 | 12/1975 | Austin, Jr. | 32/22 |

FOREIGN PATENTS OR APPLICATIONS

2,039,110   2/1972   Germany .............................. 32/22

*Primary Examiner*—Jack Q. Lever
*Attorney, Agent, or Firm*—Haseltine, Lake & Waters

[57] ABSTRACT

An arrangement for the switching on-and-off of a pressurized medium flow and, more particularly a pressurized medium flow which is conducted to a valve through a pressure medium conduit, and then further conducted from there to a withdrawing or extracting location. The valve is supported on a holder so as to be supportable thereon between two end positions, and is so constructed as to block the pressurized medium flow in one of the end positions and to release it in the other end position, and including actuating means which are coupled with the valve which, upon actuation, will displace the valve in a context of positional change thereof.

8 Claims, 4 Drawing Figures

ARRANGEMENT FOR THE SWITCHING ON-AND-OFF OF A PRESSURIZED MEDIUM FLOW

FIELD OF THE INVENTION

The present invention relates to an arrangement for the switching on-and-off of a pressurized medium flow and, more particularly, a pressurized medium flow which is conducted to a valve through a pressure medium conduit, and then further conducted from there to a withdrawing or extracting location.

DISCUSSION OF THE PRIOR ART

In a known arrangement of the above-mentioned type, which serves for the switching on-and-off of compressed air in a dental tool having a handpiece, a spring-loaded holder or support is provided for the handpiece. When the handpiece is removed from the holder, the spring presses the holder into a position in which it opens the valve stem of the valve, meaning, displacing the valve stem into a valve-opened position, so that the pressurized medium can flow towards a compressed air motor which is located in the handpiece.

In the known arrangement it is disadvantageous that the mechanism for effecting the valve actuation is relatively complicated, and that complex measures for providing valve sealing must be met in view of the exteriorly conducted valve stem. Due to the unavoidable friction between the valve stem and the guide means associated therewith, there are required relatively high actuating forces and the movable valve components become rapidly worn.

SUMMARY OF THE INVENTION

Accordingly, it is an object of the present invention to provide an arrangement of the above-mentioned type which is substantially simplified in comparison with the current state of the technology and in which, in particular, there is a reduction in the wear and actuating forces.

The foregoing object is inventively attained in that the valve is supported on a holder so as to be supportable thereon between two end positions, and is so constructed as to block the pressurized medium flow in one of the end positions and to release it in the other end position, and including actuating means which are coupled with the valve which, upon actuation, will displace the valve in a context of positional change thereof. In the present invention it is not necessary to conduct an actuating element outwardly from the interior of the valve chamber. The valve actuation is effectuated through the change in the valve position. Consequently, the wear thereof is significantly reduced in comparison with that in the state of the technology. Moreover, the actuating force may be extremely small, in particular, when the valve is supported so as to be tiltable about an axis between two end positions. A particularly simple valve structure is afforded when the valve is fundamentally constructed of a valve housing having a valve chamber, a valve seat, and a closure element movable interiorly of the valve chamber for selectively closing or opening the valve dependent upon the position of the latter.

BFIEF DESCRIPTION OF THE DRAWINGS

Further advantages and details of the invention may now be ascertained from the following detailed description of an exemplary embodiment thereof, taken in conjunction with the accompanying drawings; in which:

FIG. 1 perspectively illustrates a dental tool or apparatus which is constructed pursuant to the invention;

DETAILED DESCRIPTION

Figure 1:
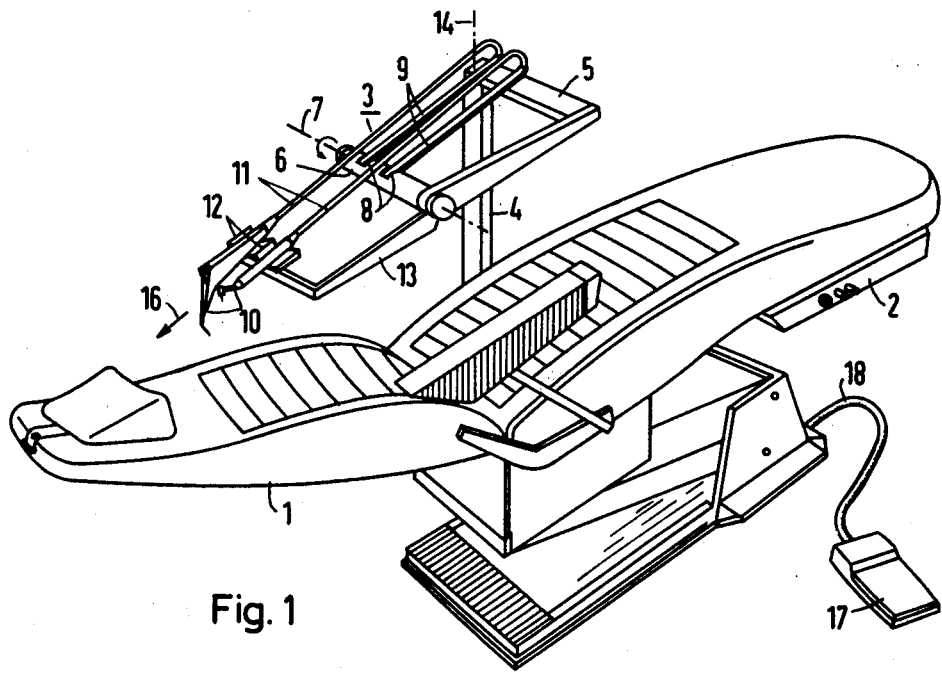

FIG. 1 illustrates a patient's support chair 1 including an associated dental tool. The dental tool consists of a supply component 2 which is supported along the lower side of the patient's support chair 1 proximate the foot end thereof, and a handpiece support or holder unit 3 pivotably supported at the side of the chair 1. Located within the supply component 2 are all of the necessary electrical and pneumatic elements which are necessary for the operation of the dental apparatus. The handpiece holder unit 3 encompasses a supporting bar 4 and an L-shaped carrying arm 5 having a roller or drum 6 connected to a forward end thereof. The drum 6 is supported on the carrying arm 5 with a cylinder axis 7 extending transverse to the extending direction (arrow 16), and includes cutouts 8 along the circumference thereof from which there project radially directed pivot arms 9. The pivot arms 9 facilitates handpieces 10 with supply conduits 11 to be brought from the illustrated rest position into an operative positon. The pivot arms 9 are so positioned interiorly of the hollow drum 6 so as to be able to be inclined in the direction of arrow 16, and possibly also minutely sidewise thereof, and to be pulled through spring force into the illustrated rest position.

For the repository of the handpieces 10 in their rest positions there is provided a frame-like handpiece holder 13, at whose free arm there are fastened repository cradles 12 for the handpieces 10. The repository cradles 12 are constructed in V-shaped configurations so that handpieces having round, as well as rectangular cross-sections can be equally readily deposited. Illustratively shown in the drawing is a handpiece for the suitable blowing out of air, water and spray, and a turbine handpiece.

The holder 13 is rigidly connected with the drum 6, and is supported on the carrying arm 5 so as to be pivotable about the cylinder axis 7. The holder 13 also serves as a grip for the displacement of the carrying arm 5 about the vertical axis 14, as well as also for the swinging of handpiece holder 13 about the cylindrical axis 7.

For operation with a handpiece, the dentist removes the pertinent handpiece from the repositing cradle and draws it in the direction of the arrow 16. The associated pivot arm 9 is thereby swung or displaced, meaning, it leaves its rest position.

The supply conduits 11 which are connected to the handpieces 10 lead from the drum 6 across the carrying arm 5 and the support bar or column 4 to the connectors in the supply component 2.

For the switching in of the media which are conveyed to the handpieces 10 there serves a foot switch 17 which is in communication with the handpieces 10 through the intermediary of a conduit 18. In the illustrated dental tool or apparatus, there is further assured that, upon actuation of the foot switch 17, no air or water will egress from the handpieces for as long as they are located in the repositing cradles 12. The foregoing is more closely elucidated hereinbelow with reference to FIG. 2 of the drawing.

Figure 2:
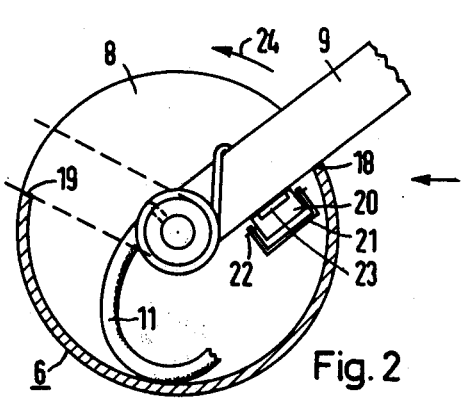
FIG. 2 is an enlarged fragmentary sectional detail of the dental tool of FIG. 1, illustrating an inventive valve.

FIG. 2 illustrates a construction for pivot arm 9 which is pivotable within the drum 6 in the recess 8 between a contact or stop 18 and a stop 19 between the illustrated rest position and the chain-dottingly drawn operative position. From FIG. 2 there may be ascertained that the supply conduit 11 leads from the pivot arm 9 through the drum 6. For effecting the control of the air flow from the supply component 2 to the handpiece 10 associated with the pivot arm 9, there serves a valve 20 which is supported in a holder 21 so as to be tiltable about an axis 22.

The holder 21 is fastened to the drum 6. In the solidly drawn rest position of the pivot arm 9, the latter presses against an actuating element 23 of the valve 20 whereby the valve 20 interrupts the compressed air flow to the therewith associated handpiece 10. When the handpiece 10 is removed from the repositing cradle 12, the pivot arm 9 is swung in the direction of arrow 24 and releases the actuating element 23. Due to gravity, the valve 20 tilts into a position in which the compressed air flow is set free from the supply component 2 to the handpiece 10. There is thus effected an automatic release of the compressed air flow when the dentist takes the handpiece 10 into his hand. The compressed air may hereby serve for a turbine drive, as spray air, or for the blowing out of tooth cavities. Each of the handpieces shown in FIG. 1 may each, respectively, have a valve 20 associated therewith. The valve 20 may hereby be also a valve unit which encompasses a plurality of individual valves, and which are supported so as to be commonly pivotable. Through the provision of a plurality of valves, for example, there may be concurrently released the drive air for the turbine and the spray air.

Figure 3:
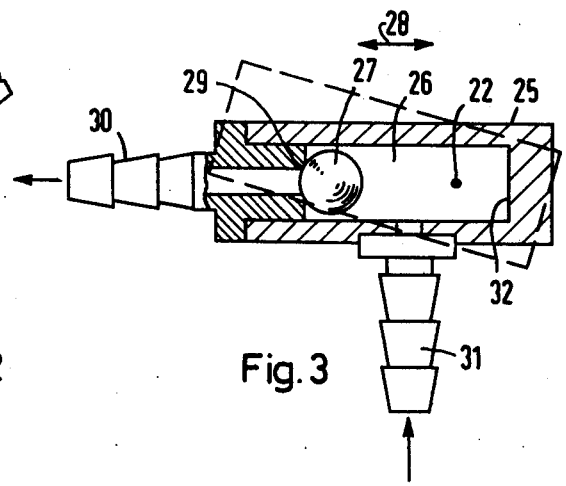
FIG. 3 is a sectional view taken through a valve constructed pursuant to the invention.

FIG. 3 illustrates the construction of a valve which is utilizable in connection with FIG. 2. The valve possesses a housing 25 which has an internal cylinder chamber 26, within which a sphere 27 is movable to and fro in the direction of two-headed arrow 28. In the one end position thereof, the sphere 27 closes off a valve seat 29 which forms the mouth of the outlet conduit 30 in the valve chamber 26 which leads to the handpiece. Communicating with the annular surface of the valve chamber 26 is a compressed air conduit 31 which leads thereto from the foot switch 17.

In the illustrated valve position, the compressed air flow from the foot switch 17 to the appropriate handpiece 10 is interrupted or blocked. When the handpiece 10 is removed from the associated cradle 12 then, in the described manner, the corresponding pivot arm 9 releases the valve. The valve tilts about axis 22 into the position shown chain-dotted in FIG. 3, in which the sphere 27 lies against the lower end 32 of the cylinder chamber 26. In this position the sphere releases the compressed air flow from the inlet conduit 31 to the outlet conduit 30 and, upon actuation of the footswitch 17, compressed air can thereby flow towards the withdrawn handpiece 10.

Figure 4:
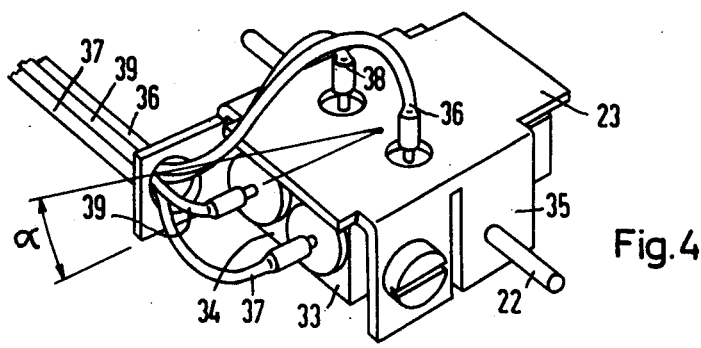
FIG. 4 is a perspective view of an arrangement with two commonly adjustable valves constructed pursuant to the invention.

FIG. 4 illustrates an arrangement with two valves 33 and 34 which are supported in a common holder 35. The valve 33 possesses an inlet conduit 36 and an outlet conduit 37, and the valve 34 an inlet conduit 38 and an outlet conduit 39. The conduits 37 and 39 lead to the pertinent handpiece. When the associated pivot arm 9 presses against the actuating element 23, the valve arrangement pursuant to FIG. 4 assumes the illustrated position, and the compressed air flow from the inlet conduits 36, 38 to the outlet conduits 37, 39 is interrupted. When the associated handpiece is then withdrawn, due to gravity the valve arrangement tilts about an angle $\alpha$ so that the spheres in the valves 33, 34 release the compressed air flow from inlet conduits 36, 38 to the outlet conduits 37, 39. The two valves pursuant to FIG. 4, for instance, may serve for the concurrent release and closure for the drive air and the spray air for a turbine handpiece.

The illustrated tilted position of the valves for the handpieces, and the utilization of valves which are actuatable upon their tilting, leads to a particularly simple construction of the valve arrangement for the handpieces. Within the scope of the invention there are also employable other valves which are actuable through change of their positions. The valve pursuant to FIG. 3, in lieu of a cylindrical valve chamber 26, may also possess a prismatic valve chamber. The sphere 27 may be replaced by a piston-like closure element.

Within the scope of the invention, the actuation of the positionally-changeably supported valve may also be carried out upon the reaching of a predetermined hose extension, for example, when the pivot arm which is associated with the handpiece assumes a predetermined angular position. Furthermore, when using a hose drum for coiling of the hose, in lieu of a pivot arm the valve may be actuated upon reaching a predetermined degree of coiling off from the drum.

What is claimed is:

1. In an arrangement for the switching on-and-off of a pressurized medium flow including a valve for receiving said flow from a pressurized medium conduit and for conducting it to an extracting location, the improvement comprising holder means for supporting said valve so as to have the positioning of the latter changeable between two end positions, said valve blocking flow of said pressurized medium in one of said end positions and permitting flow in the other of said end positions; and actuating means operatively connected with said valve so as to effect a positional change of said valve responsive to actuation of said actuating means.

2. An arrangement as claimed in claim 1, said holder supporting said valve for tilting about an axis.

3. An arrangement as claimed in claim 2, said valve being normally maintained in one said end position thereof responsive to gravity.

4. An arrangement as claimed in claim 1, said valve having a valve chamber; a valve seat at one end of said chamber communicating with an outlet conduit for said pressurized medium; an inlet conduit for said pressurized medium communicating with said chamber remote from said outlet conduit; and closure means movable within said chamber responsive to positional changes of said valve, said closure means closing off said valve seat in one position of said valve so as to block said outlet conduit and in the other position of said valve communicating said outlet conduit with said inlet conduit.

5. An arrangement as claimed in claim 4, said closure means comprising a sphere.

6. An arrangement as claimed in claim 5, said valve chamber being cylindrical, said valve seat being located at one end of said cylinder, and said inlet conduit communicating with the circumferential wall of said cylinder.

7. An arrangement as claimed in claim 1, comprising a dental tool including at least one handpiece, said valve being located in said dental tool; repository means for supporting said dental tool in a rest position so as to facilitate withdrawal therefrom into an operative position; said actuating means comprising a pivot arm having a supply conduit for said handpiece connected thereto, said valve being operatively connected with said pivot arm whereby removal of said handpiece from the rest position automatically causes said valve to release flow of said pressurized medium.

8. An arrangement as claimed in claim 7, comprising a plurality of said handpieces each having a respective number of said valves associated therewith for supplying necessary pressurized medium flows; and a tiltable positionally changeable holder means commonly mounting said plurality of valves.

* * * * *